US00PP29452P2

(12) United States Plant Patent
Van Swieten

(10) Patent No.: US PP29,452 P2
(45) Date of Patent: Jul. 3, 2018

(54) ***PHALAENOPSIS* ORCHID PLANT NAMED 'PHALDOPFO'**

(50) Latin Name: ***Phalaenopsis* hybrid**
Varietal Denomination: PHALDOPFO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/530,888

(22) Filed: Mar. 16, 2017

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALDOPFO', particularly characterized by having large, white flowers with purple blush and red-purple dots and stripes at the edge, 1 to 2 peduncles that are long and sturdy, leaves that are obovate, and is propagated by meristem tissue culture, is disclosed.

3 Drawing Sheets

Genus and species: *Phalaenopsis* hybrid.
Variety denomination: 'PHALDOPFO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALDOPFO'.

The new *Phalaenopsis* plant is a product of a planned breeding program conducted by the inventor in Bleiswijk, The Netherlands. The objective of this breeding program was to create a new *Phalaenopsis* plant with large, white flowers with purple blush and red-purple dots and stripes at the edge, suitable for potted plant production.

The new *Phalaenopsis* plant 'PHALDOPFO' is a result of cross-pollination made by the inventor in March 2005 in Bleiswijk, The Netherlands of the proprietary female, or seed parent, *Phalaenopsis* hybrid '01-5018' (unpatented) with the proprietary male, or pollen parent, *Phalaenopsis* hybrid '6133-04' (unpatented).

The new *Phalaenopsis* was selected by the inventor as a single plant within the progeny of the stated cross-pollination in a controlled greenhouse in Bleiswijk, The Netherlands in March 2008. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

'PHALDOPFO' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALDOPFO' as a new and distinct variety of *Phalaenopsis* plant.

1) Large, white flowers with purple blush and red-purple dots and stripes at the edge;
2) 1 to 2 peduncles;
3) Peduncle is long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in January 2017. Colors in the photographs may differ from the color values cited in the detailed botanical description, which accurately describe the actual colors of the new variety.

DESCRIPTION OF THE NEW VARIETY

Figure 1:
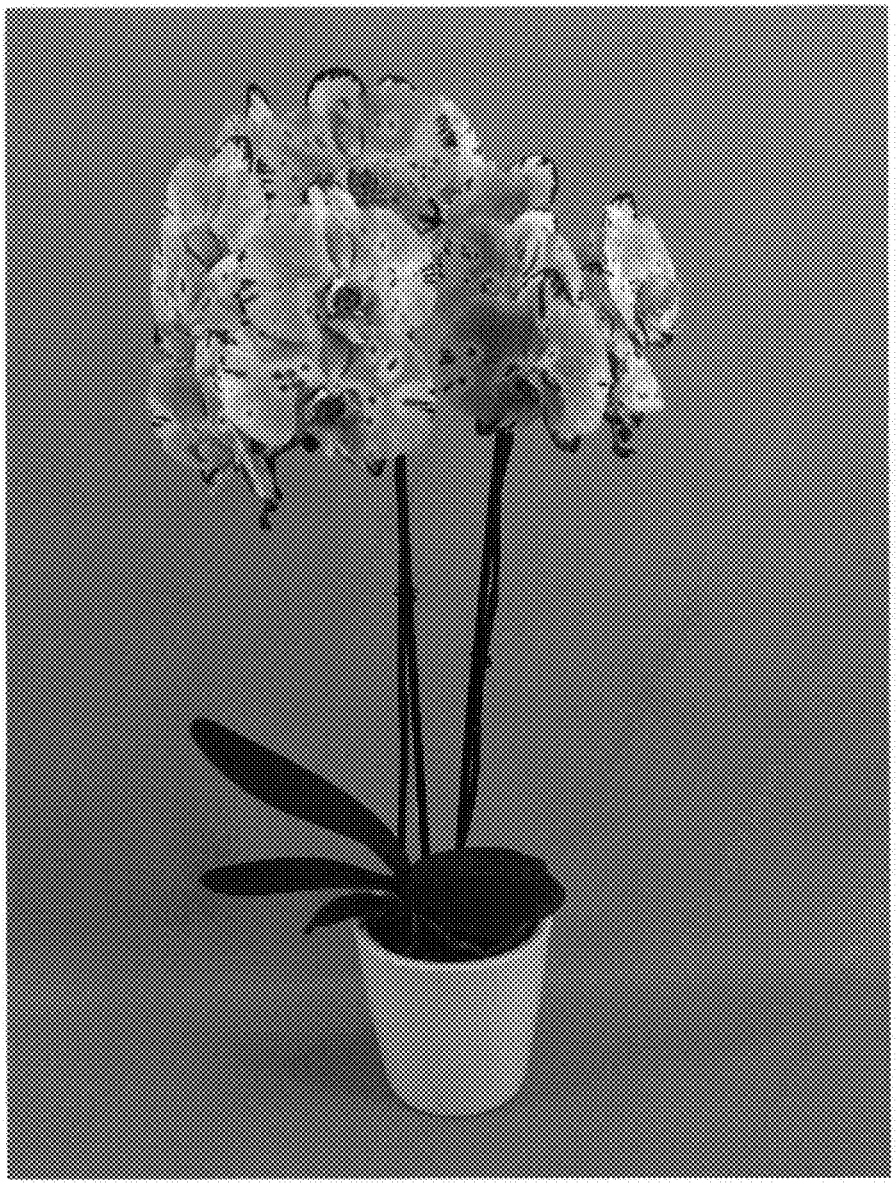
FIG. 1 shows the overall plant habit, including blooms and foliage of 'PHALDOPFO'.
Figure 2:
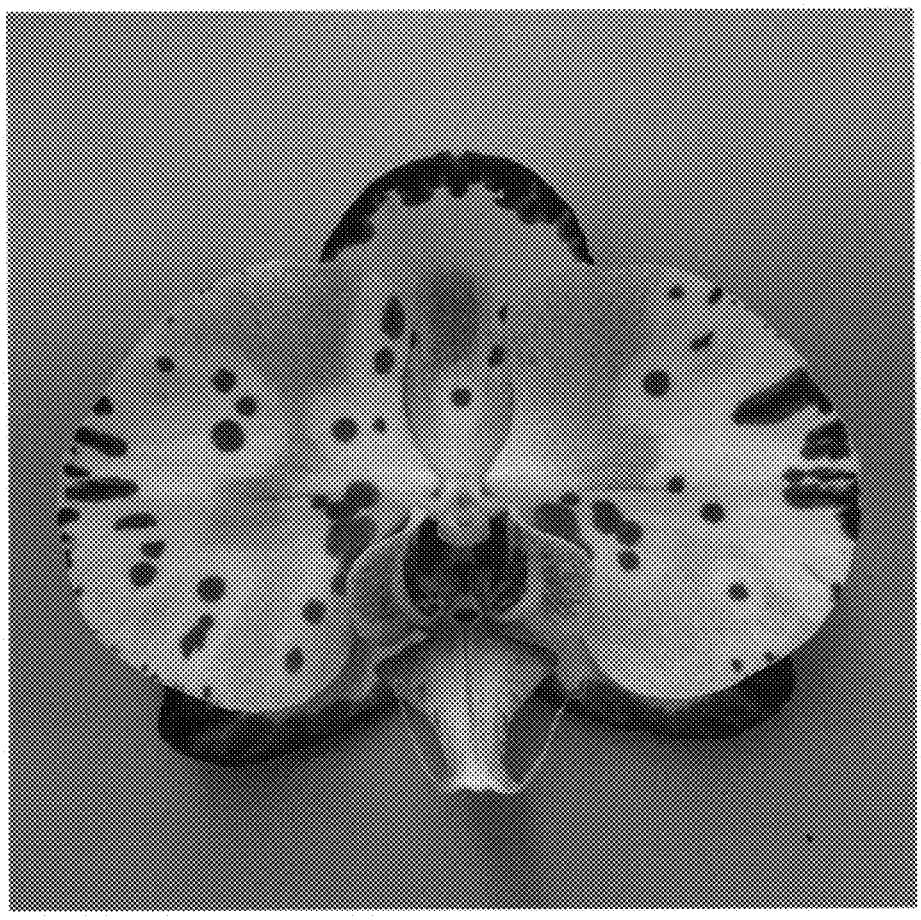
FIG. 2 shows a close-up of a flower of 'PHALDOPFO'.
Figure 3:
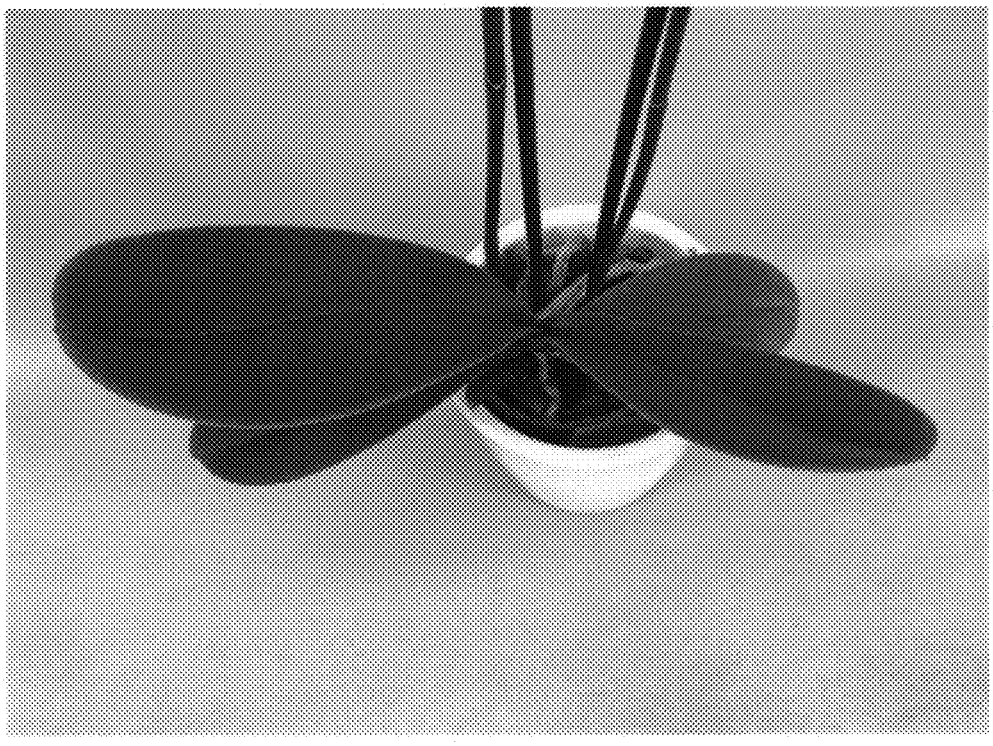
FIG. 3 shows a close-up of the leaves of 'PHALDOPFO'.

The following detailed description sets forth the distinctive characteristics of 'PHALDOPFO'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-

6000 lux natural light in a greenhouse in Bleiswijk, The Netherlands. Observations and measurements were made in January 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALDOPFO'.

Parentage:

*Female parent*.—*Phalaenopsis* cultivar '01-5018' (unpatented).

*Male parent*.—*Phalaenopsis* cultivar '6133-04' (unpatented).

Propagation:

*Type*.—Meristem tissue culture.

Roots:

*Root description*.—Greyed-green colored roots (RHS 190A/B) with branching lateral roots having light purple colored root tips (RHS 77D).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 65.0 cm to 75.0 cm.

*Width* (*measured from leaf tips*).—About 26.0 cm to 30.0 cm.

*Vigor*.—Strong.

Leaves:

*Mature leaves*.—Quantity per plant: 6 to 8 leaves are produced before flowering. Length (fully expanded): 17.0 cm to 19.0 cm. Width: 7.0 cm to 9.0 cm. Shape: Obovate. Base shape: Moderately elongated. Apex: Unequal rounded. Leaf blade angle with the petiole (measured from the horizontal position): Between 30 degrees and 40 degrees. Leaf margin: Entire. Color: Upper surface: RHS 147A. Lower surface: RHS 147B. Texture: Rough. Thickness: 2.4 mm to 2.8 mm. Venation: Pattern: Parallel. Color of the midvein: Upper surface: RHS 147A. Lower surface: RHS 147B.

Peduncle:

*Quantity per plant*.—1 to 2.

*Number of flowers per peduncle*.—8 to 15.

*Length*.—65.0 cm to 75.0 cm.

*Diameter*.—5.5 mm to 6.0 mm.

*Strength*.—Strong.

*Aspect*.—Upright to slightly pendant.

*Texture*.—Smooth.

*Color*.—Brown (RHS N200A) with a touch of green (RHS 147B).

*Internode length*.—45.0 mm to 50.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 250.0 mm to 300.0 mm.

*Flowering time*.—First flowers can be expected 10 to 11 months after planting in a 12 cm (diameter) pot.

*Flower*.—Height: 90.0 mm to 95.0 mm. Diameter: 105.0 mm to 110.0 mm. Depth of lip: 25.0 mm to 27.0 mm.

*Flower longevity*.—On the plant: 15 to 19 weeks.

*Fragrance*.—Absent.

*Flower bud*.—Average size: Large. Length: 26.0 mm to 28.0 mm. Width: 22.0 mm to 24.0 mm. Shape: Egg shaped. Color: Green (RHS 145B) and diluting red-purple (RHS 71A).

*Petals*.—Arrangement: Open/free. Shape: Semi-circular. Apex: Rounded asymmetric. Margin: Slightly undulated. Length (from base to tip): 51.0 mm to 53.0 mm. Width: 64.0 mm to 66.0 mm. Color (when fully opened): Upper surface: Basic color: White (RHS NN155C). Over color: Purple (RHS N78C) with dots and stripes (RHS N79C/D) at the edge. Lower surface: Basic color: White (RHS NN155C). Over color: Purple (RHS N78D) with diluting dots (RHS N79C/D).

*Dorsal sepal*.—Shape: Broad elliptic. Apex: Rounded to slightly emarginated equal. Margin: Slightly undulated. Length (from base to tip): 50.0 mm to 52.0 mm. Width: 40.0 mm to 42.0 mm. Color (when fully opened): Upper surface: Basic color: White (RHS NN155C). Over color: Purple (RHS N78C) with edge and dots (RHS N79C/D). Lower surface: Basic color: White (RHS NN155C). Over color: Purple (RHS N78C) and diluting edge (RHS N79B/C).

*Lateral sepals*.—Shape: Ovate. Apex: Obtuse asymmetric. Margin: Entire. Length (from base to tip): 49.0 mm to 51.0 mm. Width: 30.0 mm to 32.0 mm. Color (when fully opened): Upper surface: Basic color: White (RHS NN155C). Over color: Green (RHS 145C) at the base and red-purple dots (RHS N79D) and stripes at the edge (RHS N79B/C). Lower surface: Basic color: White (RHS NN155C). Over color: Green (RHS 145C) at the base; purple blush (RHS N78D) and diluting edge (RHS N79C).

*Labellum* (*lip*).—Whiskers: Present. Length of whiskers: 19.0 mm to 21.0 mm. Color of whiskers: White (RHS NN155C) with purple stripe (RHS N77B) at the middle. Pubescence on the lip: Absent.

*Lateral lobe*.—Shape: Spatulate. Margin: Undulated. Length: 22.0 mm to 24.0 mm. Width: 16.0 mm to 18.0 mm. Color: White (RHS NN155C) with purple edge (RHS N78D); yellow region on one side (RHS 7B) and red stripes at the base (RHS 183C).

*Apical lobe*.—Shape: Triangular. Margin: Entire. Length: 20.0 mm to 22.0 mm. Width: 24.0 mm to 26.0 mm. Color: White (RHS NN155C) and light purple (RHS 76C); red at the base (RHS 183D) and yellow (RHS 7B) toward the wings.

*Callus*.—Height: 0.6 cm to 0.7 cm. Length: 0.6 cm to 0.7 cm. Width: 0.4 cm to 0.5 cm. Color: Yellow (RHS 8A) dotted (RHS 183B).

Reproductive organs:

*Column*.—Length: 9.0 mm to 11.0 mm. Diameter: 5.7 mm to 6.0 mm. Color: White (RHS NN155C) with purple region (RHS N78A) at the middle.

*Pollinia*.—Quantity: 2. Diameter: 1.0 mm to 1.2 mm. Color: Orange (RHS 26A).

*Ovary*.—Length: 9.0 mm to 11.0 mm. Diameter: 2.6 mm to 2.8 mm.

*Pedicel*.—Length: 39.0 mm to 41.0 mm. Diameter: 3.0 mm to 3.2 mm. Color: Green (RHS 146C) and light purple (RHS 76D) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND SIMILAR COMMERCIAL VARIETIES

'PHALDOPFO' differs from female parent plant '01-5018' (unpatented), also known as 'PHALCOSBAP', in that 'PHALDOPFO' has a white and light purple apical lobe with red at the base and yellow toward the wings, a dotted and striped with blush flower pattern, and a yellow callus with dots, whereas '01-5018' has an apical lobe with yellow at the base and red-purple toward the whiskers, an edged flower pattern, and a dark red callus. Additionally, 'PHALDOPFO' has larger flowers and longer whiskers than '01-5018'.

'PHALDOPFO' differs from male parent plant '6133-04' (unpatented), also known as 'PHALBOXI', in that 'PHALDOPFO' has a white and light purple apical lobe with red at the base and yellow toward the wings, a dotted and striped with blush flower pattern, and a yellow (RHS 8A) callus with dots (RHS 183B), whereas '6133-04' has an apical lobe with yellow-green at the base and white toward the whiskers, an even flower pattern, and a yellow (RHS 9A) callus with dots (RHS 176B). Additionally, 'PHALDOPFO' has larger flowers and shorter whiskers than '6133-04'.

'PHALDOPFO' is most similar to the commercial *Phalaenopsis* plants named 'PHALFOYX' (U.S. Plant Pat. No. 28,103) and 'PHALDASYH' (U.S. Plant Pat. No. 27,341). 'PHALDOPFO' differs from the commercial variety 'PHALFOYX' in that 'PHALDOPFO' has a yellow callus with dots and white whiskers with a purple stripe in the middle, whereas 'PHALFOYX' has a dark red callus and dark red whiskers with yellow tips. Additionally, 'PHALDOPFO' has larger flowers and longer whiskers than 'PHALFOYX'.

'PHALDOPFO' differs from the commercial variety 'PHALDASYH' in that 'PHALDOPFO' has white flowers, a yellow callus with dots and white whiskers with a purple stripe in the middle, whereas 'PHALDASYH' has yellow flowers, a dark red callus and purple whiskers. Additionally, 'PHALDOPFO' has larger flowers and much longer whiskers than 'PHALDASYH'.

I claim:

1. A new and distinct variety of *Phalaenopsis* plant named 'PHALDOPFO', substantially as described and illustrated herein.

* * * * *